United States Patent
Gaylord

(10) Patent No.: US 10,383,404 B2
(45) Date of Patent: *Aug. 20, 2019

(54) LACE-TONGUE ATTACHMENT FOR ANKLE STABILIZING DEVICE

(71) Applicant: Eric Lee Gaylord, Matthews, NC (US)

(72) Inventor: Eric Lee Gaylord, Matthews, NC (US)

(73) Assignee: MEDICAL SPECIALTIES, INC., Charlotte, NC (US)

( * ) Notice: Subject to any disclaimer, the term of this patent is extended or adjusted under 35 U.S.C. 154(b) by 475 days.

This patent is subject to a terminal disclaimer.

(21) Appl. No.: 15/164,000

(22) Filed: May 25, 2016

(65) Prior Publication Data

US 2016/0262498 A1 Sep. 15, 2016

Related U.S. Application Data

(63) Continuation of application No. 14/461,695, filed on Aug. 18, 2014, now Pat. No. 9,375,339, which is a continuation of application No. 13/363,691, filed on Feb. 1, 2012, now Pat. No. 8,808,215.

(51) Int. Cl.
*A43C 11/20* (2006.01)
*A61F 5/01* (2006.01)

(52) U.S. Cl.
CPC ............ *A43C 11/20* (2013.01); *A61F 5/0104* (2013.01); *A61F 5/0111* (2013.01)

(58) Field of Classification Search
CPC ...... A43C 11/20; A61F 5/0104; A61F 5/0111; A61F 5/0113; A61F 5/0116; A61F 5/0118; A61F 5/0127; A61F 5/0195; A61F 13/066; A61F 5/0585; A61F 5/0109; A61F 15/006; A61F 2/6607

See application file for complete search history.

(56) References Cited

U.S. PATENT DOCUMENTS

| | | | |
|---|---|---|---|
| 4,255,876 A * | 3/1981 | Johnson | A43B 5/00 36/129 |
| 4,313,433 A * | 2/1982 | Cramer | A43B 7/1495 602/27 |
| 4,440,158 A * | 4/1984 | Shapiro | A61F 5/0111 602/27 |
| 4,442,613 A | 4/1984 | Dobbin | |
| 4,597,198 A | 7/1986 | Schweitzer | |
| 4,811,500 A | 3/1989 | Maccano | |
| 4,899,466 A | 2/1990 | Skaja | |
| 5,067,486 A | 11/1991 | Hely | |
| 5,402,589 A | 4/1995 | Lubrani | |
| 5,659,979 A | 8/1997 | Sileo | |
| 5,741,222 A * | 4/1998 | Fiore | A61F 5/0106 602/23 |
| 5,795,316 A | 8/1998 | Gaylord | |
| 6,112,379 A | 9/2000 | Fernandez | |

(Continued)

*Primary Examiner* — Ophelia A Hawthorne
(74) *Attorney, Agent, or Firm* — Additon, Higgins & Pendleton, P.A.

(57) ABSTRACT

An ankle stabilizing device having a lace-tongue attachment includes a body member, a plurality of eyelets extending along the front edges of the body member, and a centering lace. The centering lace is secured to the ankle stabilizing device between the pair of eyelets at the toe-end of the device such that the central portion of the centering lace is precluded from passing through either of the toe-end pair of eyelets.

24 Claims, 4 Drawing Sheets

(56) References Cited

U.S. PATENT DOCUMENTS

| | | | |
|---|---|---|---|
| 6,158,096 A | 12/2000 | Bar | |
| 6,973,744 B2 | 12/2005 | Curet | |
| 7,497,839 B2 * | 3/2009 | Quinn | A61F 5/0111 602/23 |
| 7,651,472 B2 | 1/2010 | Gaylord et al. | |
| 8,808,215 B2 * | 8/2014 | Gaylord | A61F 5/0111 128/882 |
| 9,375,339 B2 * | 6/2016 | Gaylord | A61F 5/0111 |
| 2005/0288615 A1 | 12/2005 | Gaylord | |
| 2009/0112410 A1 | 4/2009 | Gaylord et al. | |
| 2014/0358056 A1 | 12/2014 | Gaylord | |

* cited by examiner

LACE-TONGUE ATTACHMENT FOR ANKLE STABILIZING DEVICE

CROSS-REFERENCE TO PRIORITY APPLICATION

This application is a continuation of commonly assigned U.S. patent application Ser. No. 14/461,695 for a "Lace-Tongue Attachment for Ankle Stabilizing Device" (filed Aug. 18, 2014, and published Dec. 4, 2014, as Publication No. 2014/0358056 A1), now U.S. Pat. No. 9,375,339.

Parent U.S. patent application Ser. No. 14/461,695 is itself a continuation of commonly assigned U.S. patent application Ser. No. 13/363,691 for a "Branded Lace-Tongue Attachment for Ankle Stabilizing Device" (filed Feb. 1, 2012, and published Aug. 1, 2013, as Publication No. 2013/0197412 A1), now U.S. Pat. No. 8,808,215.

Each of the foregoing patent applications and publications is hereby incorporated by reference in its entirety.

BACKGROUND OF THE INVENTION

The present invention relates to the field of ankle stabilizing devices, and more specifically, to ankle stabilizing devices that utilize a lace-eyelet type fastener to secure a foot and ankle within the device.

As known to participants in athletics, the ankle is often injured as a result of contact with other participants or items of equipment, or as a result of the ankle assuming an unnatural position during play. Injuries typically occur during motions typically associated with athletics such as running, jumping, falling, or the like. Specifically, ankles are particularly vulnerable to sprains, fractures, and the like.

Athletes at risk for ankle injuries often utilize some form of ankle support during participation in sporting events. A large number of ankle injuries occur when the foot rolls or falls inwardly (referred to as "inversion") when the outer, or lateral, ligaments are stretched too far, or outwardly (referred to as "eversion") when the inner ligament (i.e., deltoid ligament) is stretched too far. Many athletes rely upon taping to provide supplemental ankle support, whereby the athlete or trainer winds athletic tape around the athlete's ankle to thereby limit the motion of the ankle relative to the leg. Although taping stabilizes the ankle against undesired motion, a number of drawbacks exist. For example, taping may restrict all motion of the ankle, both desirable and undesirable. The restrictive characteristics of taping thus hinder the athlete's ability to perform. Further, tape tends to stretch and loosen as the athlete moves, thereby decreasing its effectiveness in supporting the ankle.

Known stabilizing devices include boot-shaped members or sleeves which cover the athlete's foot and ankle and include supplemental straps designed to wrap around and stabilize certain areas of the individual's foot and ankle. Many known stabilizing devices include a lace-eyelet type fastener to secure a foot and ankle within the device. The laces are typically threaded through the eyelets and the device may be tightened around the foot and ankle by pulling on the laces.

Lace-eyelet type fasteners have been utilized in the shoe and boot industry for decades. In the context of shoes and boots, lace-eyelet type fasteners present a few problems that have been identified including the ability of the laces to slip or loosen in the eyelets and the ability of the shoe or boot's tongue to slide underneath the laces. Various solutions have been employed to prevent these problems.

For example, U.S. Pat. No. 4,899,466 describes a lacing system that includes locking eyelets located at the upper end of the shoe (i.e., towards the ankle rather than towards the toe end of the foot). The locking eyelets help to prevent the laces from slipping or loosening.

U.S. Pat. No. 4,442,613 describes a shoe tongue holder assembly designed to prevent the tongue of a shoe from sliding. The shoe tongue holder assembly includes hook and loop fasteners at the upper end of the shoe.

U.S. Pat. No. 5,402,589 describes an apparatus that secures both the laces and tongue of a shoe to prevent loosening of the laces and slipping of the tongue. The shoe-wearer first ties a knot in the shoelaces and then clamps the two jaws of the apparatus around the knot. The apparatus is secured to the upper end of the tongue where the laces are tied.

U.S. Pat. No. 6,158,096 describes an assembly to secure the tongues of lace-type shoes in a stationary position. The assembly is placed at the upper end of the tongue because the toe-end of the tongue is secured to the shoe. The assembly requires a special lacing configuration to secure the placement of the tongue.

Thus, a variety of solutions have been proposed for the problems associated with lace-type fasteners that are specific to shoes or boots. In the context of ankle stabilizing devices, however, utilizing a lace-eyelet type fastener presents a unique set of problems that none of the previously discussed documents address.

For example, ankle stabilizing devices typically use lace-type fasteners that extend up the ankle to the lower portion of the leg (i.e., higher up the leg than typical shoes). Thus, unlike lace-up shoes or boots, lace-up ankle brace removal involves unlacing all but the last few rows of the paired eyelets each and every time the ankle brace is removed. The brace removal process is often done with haste whereby the user quickly "whips" the laces out of enough of the eyelets to slide the brace off of the foot and ankle.

The typical ankle stabilizing device removal process leaves the lace uncentered because a significant portion, if not a majority, of the lace has been loosened from the eyelets. The uncentered positioning of the lace is generally only discovered after a subsequent user completely re-laces the brace and attempts to tie the lace. The user must then unlace the brace, center the lace, and re-lace the brace prior to use. This process is time consuming and frustrating for the subsequent user. The previously discussed documents fail to provide a solution to this problem because they impede typical fitting, use, removal, and refitting of an ankle stabilizing device.

Therefore, a need exists for an ankle stabilizing device that includes a lace-eyelet type fastener and facilitates the fitting, use, removal, and refitting of an ankle stabilizing device.

SUMMARY OF THE INVENTION

In one aspect, the invention embraces an ankle stabilizing device that includes a body member having an upper portion, a lower portion, a front portion, a rear portion, a first side, a second side, an interior surface, and an exterior surface. The body member's first and second sides have free front edges. The ankle stabilizing device includes a plurality of eyelets extending along the free front edges of the first and second sides. The plurality of eyelets includes a toe-end pair of eyelets positioned toward the lower portion of the body member. The ankle stabilizing device further includes a centering lace having two ends and an attachment point defining two substantially equivalent lengths of the centering lace that extend from the attachment point to each of the centering lace's ends. The centering lace's attachment point secures the centering lace to the ankle stabilizing device such that the attachment point is precluded from passing through either of the toe-end pair of eyelets In another exemplary embodiment, the ankle stabilizing device includes a tongue positioned between the free front edges of the first and second sides. The centering lace's attachment point may secure the centering lace to the tongue. The tongue may be made of a mesh fabric.

In yet another exemplary embodiment, the centering lace's attachment point secures the centering lace to the ankle stabilizing device via stitched threads. The stitched threads may be stitched in such a manner as to depict a trademark or design.

In yet another exemplary embodiment, the centering lace's attachment point secures the centering lace to the first side's free front edge and/or the second side's free front edge. The centering lace's attachment point may secure the centering lace via stitched threads.

In yet another exemplary embodiment, the body member is fabricated from substantially inelastic material.

In yet another exemplary embodiment, the body member is a one-piece body member.

In yet another exemplary embodiment, the body member is a multi-piece body member.

In another aspect, the invention embraces an ankle stabilizing device that includes a body member having an upper portion, a lower portion, a front portion, a rear portion, a first side, a second side, an interior surface, and an exterior surface. The first and second sides have free front edges. The ankle stabilizing device includes a plurality of eyelets extending along the free front edges of the first and second sides. The plurality of eyelets includes a toe-end pair of eyelets positioned toward the lower portion of the body member. The ankle stabilizing device further includes a centering lace having two ends and a central portion defining two substantially equivalent lengths of the centering lace that extend from the central portion to each of the centering lace's ends. The ankle stabilizing device also includes a centering piece secured to the centering lace and the ankle stabilizing device such that the centering lace's central portion is precluded from passing through either of the toe-end pair of eyelets.

In an exemplary embodiment, the ankle stabilizing device includes a tongue positioned between the free front edges of the first and second sides. The centering piece may secure the centering lace to the tongue (e.g., via stitched threads). The stitched threads may be stitched in such a manner as to depict a trademark or design. The tongue may be made of a mesh fabric.

In yet another exemplary embodiment, the centering piece secures the centering lace to the first side's free front edge and/or the second side's free front edge. The centering piece may secure the centering lace via stitched threads.

In yet another exemplary embodiment, the body member is fabricated from substantially inelastic material.

In yet another exemplary embodiment, the body member is a one-piece body member.

In yet another exemplary embodiment, the body member is a multi-piece body member.

BRIEF DESCRIPTION OF THE DRAWINGS

The foregoing and other objects and advantages of the invention and the manner in which the same are accomplished will become clearer based on the following detailed description taken in conjunction with the accompanying drawings in which.

DETAILED DESCRIPTION OF THE INVENTION

The invention will now be described more fully hereinafter with reference to the accompanying drawings, in which multiple embodiments of the invention are shown. This invention may, however, be embodied in different forms and should not be construed as limited to the embodiments set forth herein. Rather, these embodiments are provided so that this disclosure will be thorough and complete and will fully convey the scope of the invention to those skilled in the art. Like numbers refer to like elements throughout. Further, like numbers with the prime notation refer to like or similar elements of the structure.

Figure 1:
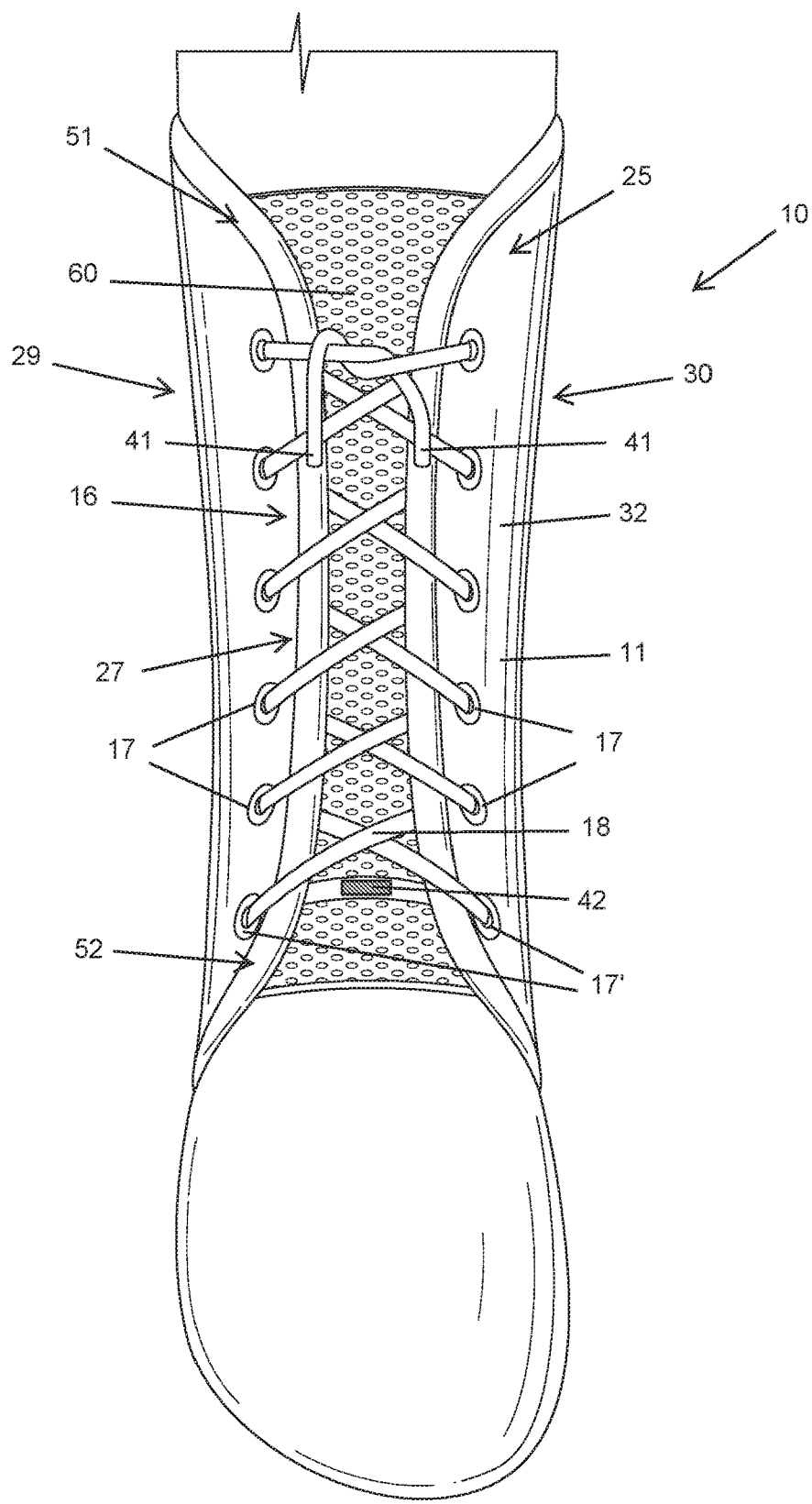
FIG. 1 is a frontal perspective view of an exemplary embodiment of the ankle stabilizing device according to the present invention.

The present invention embraces an ankle stabilizing device. In exemplary embodiments, the ankle stabilizing device has a branded lace-tongue attachment. An overall view of an embodiment of an ankle stabilizing device of the invention is set forth in the perspective view of FIG. 1. The device 10 may be worn without an athletic sock such that interior surfaces of the device 10 contact skin of the individual. Alternatively, the device 10 may be worn over an athletic sock such that interior surfaces of the device 10 contact the sock. Further, the device 10 is configured for wear on the right or left foot. Therefore, FIG. 1 illustrates the device 10 as it appears when worn on a right foot. When worn on a left foot, the device 10 would be a mirror-image version of the one illustrated in FIG. 1.

The ankle stabilizing device 10 includes a body member 11 for receiving a foot and/or ankle. The body member 11 has free front edges (e.g., a left front edge and a right front edge). A "free edge" refers to an edge that does not intersect with another surface or portion of the device 10.

Figure 2:
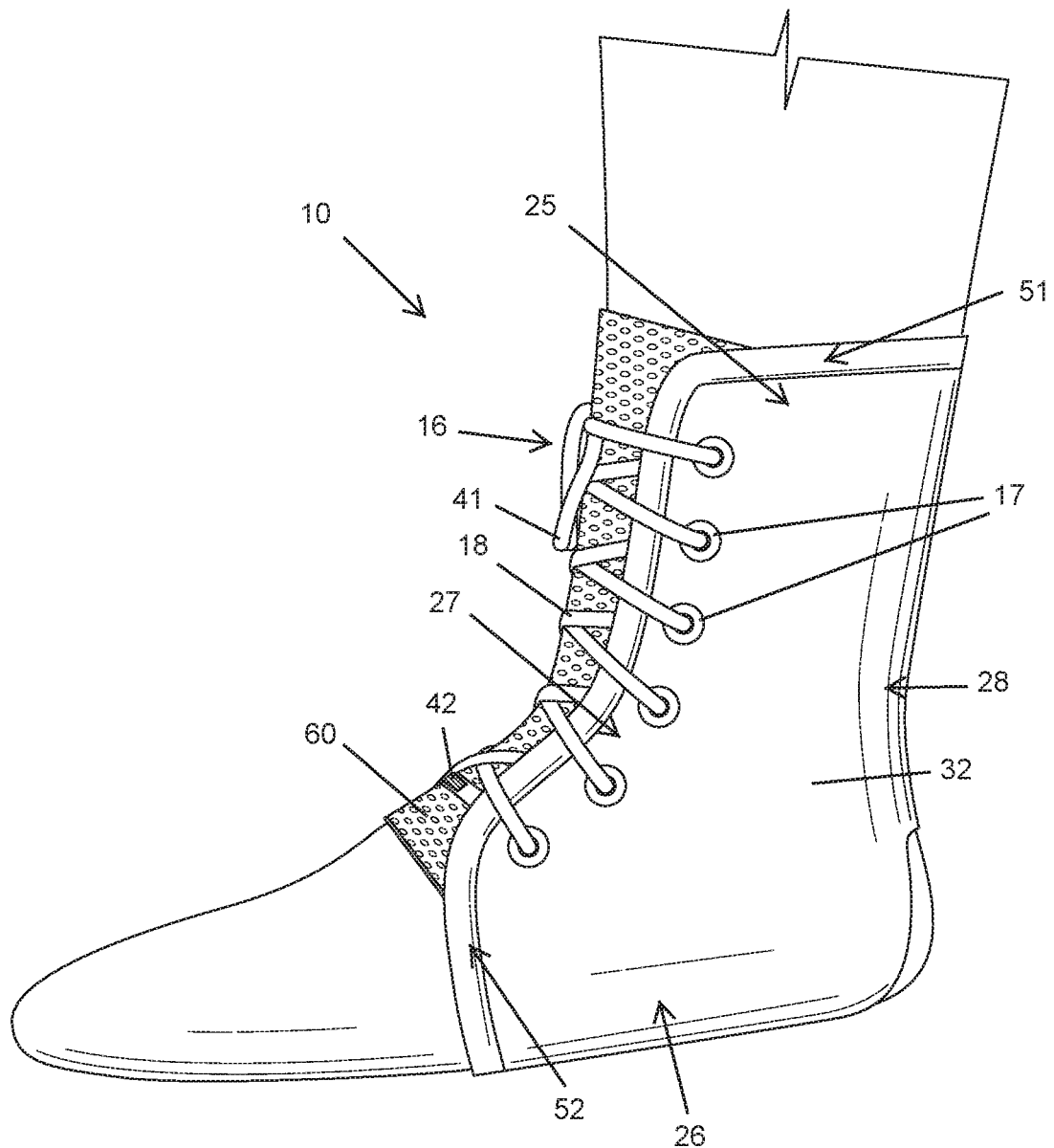
FIG. 2 is a perspective view of an exemplary embodiment of the ankle stabilizing device according to the present invention.

The body member 11 is shaped to receive a foot and ankle, and defines an upper portion 25, a lower portion 26, a front portion 27, and a rear portion 28. Referring to FIG. 2, it will be understood that the term "portion" refers to various areas of the device 10. It will be further understood that the terms "upper portion" and "lower portion" may also refer to "lower portion" and "upper portion," respectively, dependent upon the perspective of the individual viewing the device 10. It will also be appreciated that the term "upper" implies the opposite of "lower." It will also be understood that the terms "front portion" and "rear portion" may also refer to "rear portion" and "front portion," respectively, dependent upon the perspective of the individual viewing the device 10. It will also be appreciated that the term "front" implies the opposite of "rear." The body member 11 also has an upper end 51 and a toe end 52. It will be understood that the term "upper end" refers to the portion of the body member 11 generally located around an ankle when worn. It will also be understood that the term "toe end" refers to the portion of the body member 11 located near the toes of a foot when worn.

As depicted in FIG. 1, the body member 11 also includes a first side 29, a second side 30, and an exterior surface 32. The body member 11 also includes an interior surface (not shown). With reference to the orientation of the brace in FIG. 2, it will be understood that the terms "interior surface" and "exterior surface" may be referred to as "inside surface" and "outside surface." Stated differently, as used herein the term interior surface implies the side of the device 10 closest to the ankle or foot of the wearer. Thus, it will be understood that the term exterior surface 32 implies the side of the device 10 opposite the interior surface (i.e., the side farthest from the ankle or foot of the wearer).

The body member 11 may be fabricated from a pliable fabric material. Advantageously, the pliable fabric material will conform to an ankle, yet minimize any stretching familiar to elastic material. As used herein, it will be understood that the term "elastic" refers to material that is capable of being easily stretched or expanded, and resuming its former shape. Stated differently, the term elastic implies the property of resisting deformation by stretching.

One embodiment of the invention provides a body member 11 fabricated from substantially inelastic fabric material. In a related aspect, it will be understood that the term "inelastic" refers to material that resists stretching and elongation. In this particular embodiment of the invention, the substantially inelastic material is a woven ballistic nylon fabric, as such fabrics have been found to be light weight, while providing a high degree of strength and durability. In addition, such fabrics are generally thin, a particularly desirable characteristic when an individual utilizes the device 10 inside a shoe (not shown).

The sheet of material forming the body member 11 may be formed from one or more sheets of fabric material. In one embodiment, the body member 11 is formed from one sheet of material that is capable of forming a boot-like shape. In this embodiment, the body member 11 may be referred to as a "one-piece" body member. The sheet of material is desirably folded and seamed to form a substantially cylindrical L-shaped configuration for covering at least a lower and rear portion of the individual's foot and ankle. In one embodiment of the body member 11, a single sheet of fabric material is secured (e.g., stitched) at the lower portion 26 of the body member 11 (i.e., under the arch of the foot). In another embodiment, the single sheet is secured at a rear portion 28 of the body member 11 (i.e., along the Achilles tendon area of the lower leg). In yet another embodiment, the body member 11 is formed from two sheets of fabric material (i.e., a "multi-piece" body member) wherein the two sheets are secured at the lower portion 26 and rear portion 28 of the body member 11. In yet another embodiment, the body member 11 may be formed from a plurality of sheets secured at one or more portions of the body member 11.

In one embodiment, the flexible body member 11 is a boot-like body member that is substantially L-shaped and covers at least a lower and rear portion of the individual's foot and ankle. In this embodiment, the body member 11 includes a stirrup portion that conforms to the lower surfaces of the foot by extending under portions of the calcaneous. The body member 11 of this embodiment defines at least one opening for receiving a portion of a heel.

It will be understood, however, that alternative embodiments of the device (not shown) may include a body member 11 without a stirrup portion. In other words, an alternative embodiment of the body member 11 has a lower edge that may end immediately below the malleoli such that the body member 11 does not extend under the foot. In this alternative embodiment, the body member 11 does not include an opening for receiving a portion of a heel.

As depicted in FIGS. 1, 2, 3, and 4, a tongue 60 may be positioned between the opposing free front edges of the body member 11. The tongue 60 may be composed of a padded fabric or a mesh fabric. The tongue 60 assists to secure the body member 11 to the foot of the individual, and provides padding between the lace 18 and the individual's foot.

With reference to FIG. 1, the ankle stabilizing device 10 further provides a body member connector 16 for securing free front edges of body member 11 to one another. The body member connector 16 facilitates the drawing of the front edges of the body member 11 towards one another to secure the device 10 about the ankle and foot. Typically, the body member connector 16 includes a plurality of eyelets 17 defined by and extending along front edges of the body member 11 and at least one centering lace 18 threaded through the respective eyelets 17. It will be understood, however, that the body member connector 16 may include any number of devices capable of drawing the front edges of the body member 11 together. A toe-end pair of eyelets 17' is positioned on the front edges at the toe end 52 of the body member 11.

Figure 3:
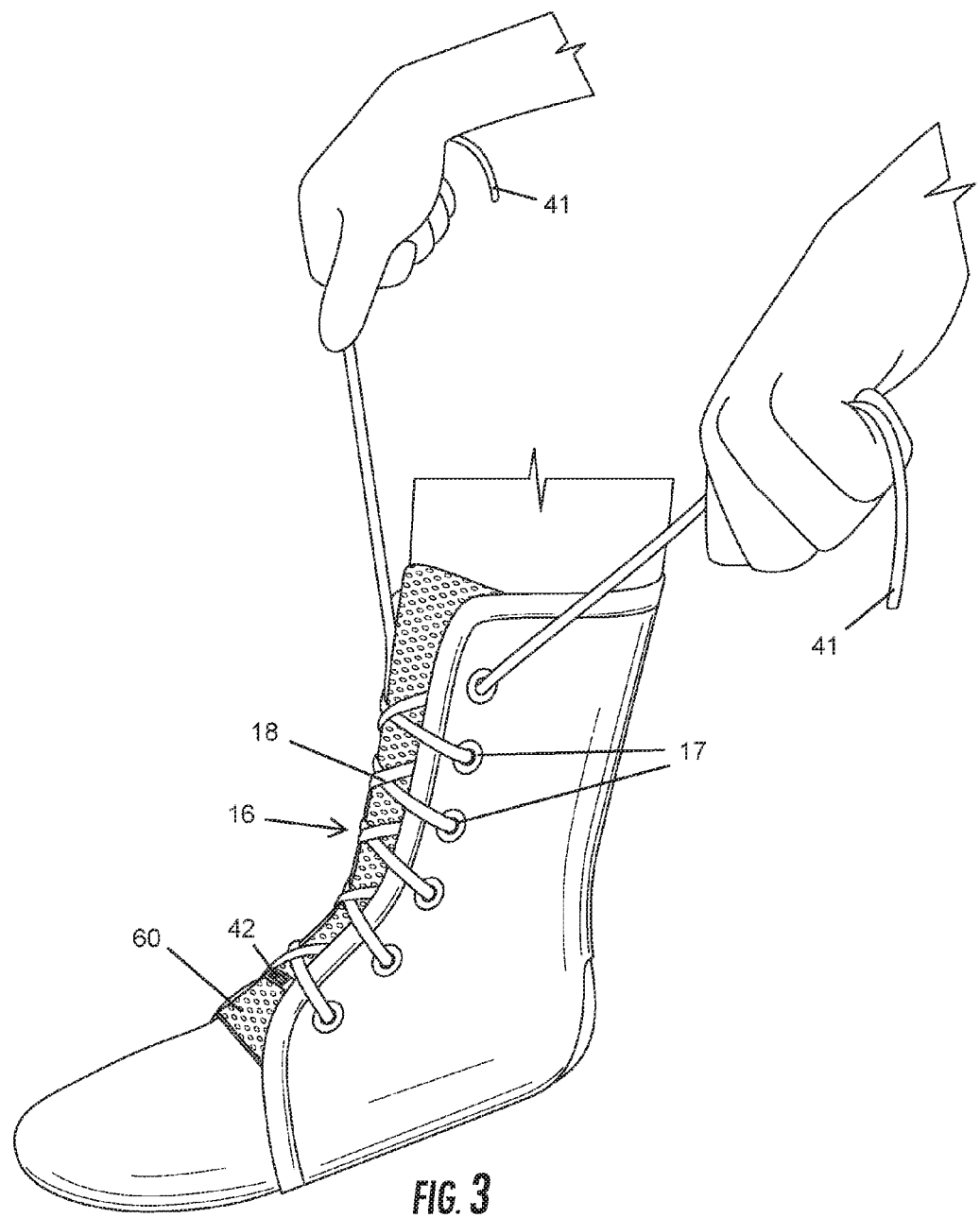
FIG. 3 is a perspective view of an exemplary embodiment of the ankle stabilizing device according to the present invention in use.

In an exemplary embodiment, the centering lace 18 has two ends 41 and an attachment point 42. For example, FIGS. 1 and 3 depict a centering lace 18 having two ends 41 and an attachment point 42. Typically, the attachment point 42 is located at the centermost portion of the centering lace 18. In other words, the centering lace's attachment point 42 defines two substantially equivalent lengths of the centering lace 18 extending from the attachment point 42 to each of the centering lace's ends 41. The centering lace's attachment point 42 typically secures the centering lace 18 to the body member 11 or the tongue 60 such that the centering lace's centermost portion and/or the attachment point 42 is precluded from passing through either of the toe-end pair of eyelets 17'.

Figure 4:
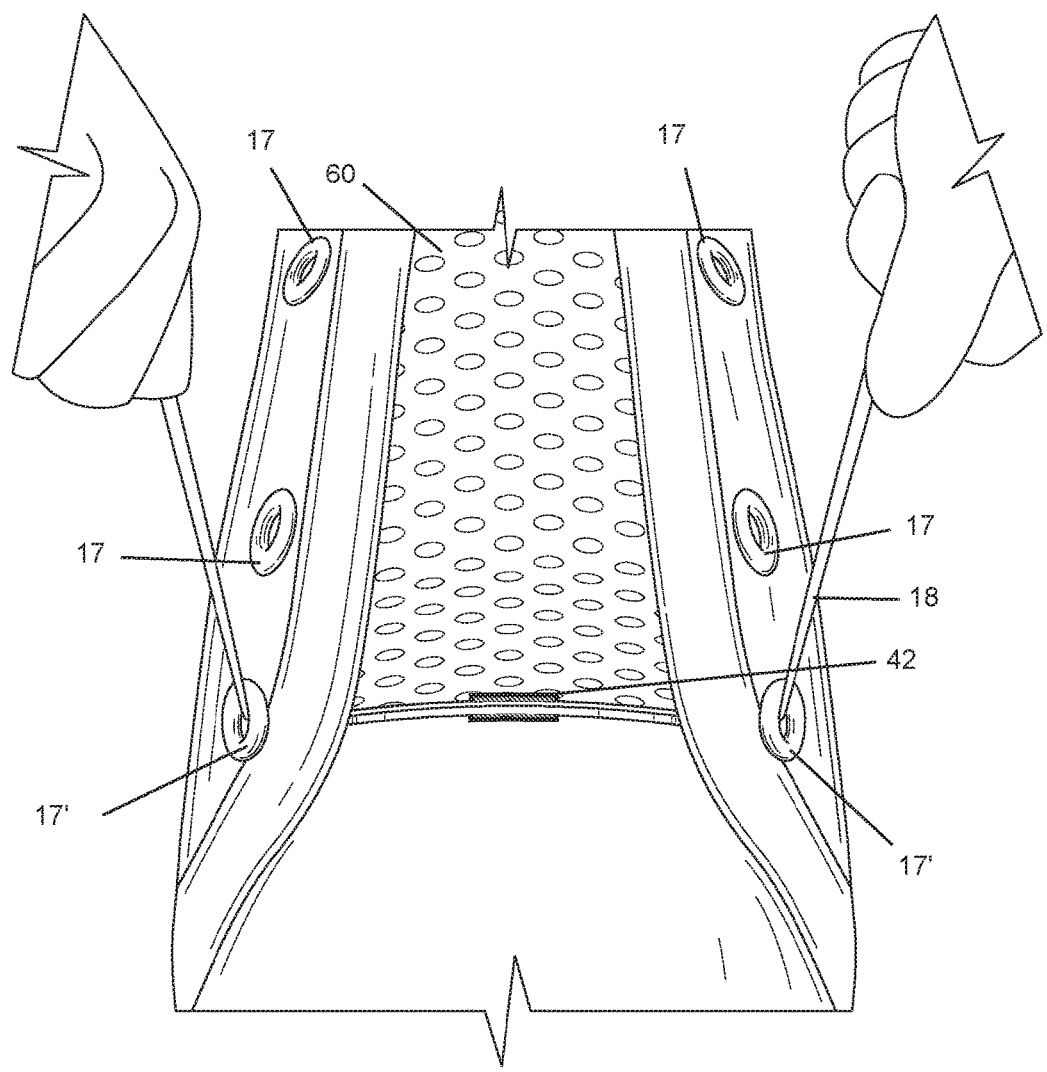
FIG. 4 is an enlarged, partial, front perspective view of an exemplary embodiment of the ankle stabilizing device according to the present invention in use.

In exemplary embodiments, the attachment point 42 is attached to the tongue 60 between the toe-end pair of eyelets 17'. The centering lace 18 may be attached to the tongue 60 via stitched threads, such as an embroidered trademark, logo, and/or design. For example, FIG. 4 depicts attachment point 42 as stitched threads extending through the tongue 60 and the centering lace 18 between the toe-end pair of eyelets 17'.

In such exemplary embodiments, the centering lace may be considered a lace-tongue attachment or a branded lace-tongue attachment. Those of ordinary skill in the art will recognize, however, that the terms "lace-tongue attachment" and "branded lace-tongue attachment" may describe a variety of centering laces that secure the centering lace's centermost portion to preclude it from passing through either of the toe-end pair of eyelets. Thus, a centering lace may be considered a lace-tongue attachment even though the centering lace is secured to a portion of the ankle stabilizing device other than a tongue.

In other exemplary embodiments, the centering lace's attachment point 42 secures the centering lace 18 to one or both of the front edges of the body member 11. Again, the centering lace 18 may be attached to the edge or edges via stitched threads, such as an embroidered trademark, logo, and/or design.

In a further exemplary embodiment, the ankle stabilizing device 10 includes a centering lace 18 having two ends 41 and a central portion. The central portion defines two substantially equivalent lengths of centering lace 18 that extend from the central portion to each of the centering lace's ends 41. The ankle stabilizing device 10 also includes a centering piece that is secured to the centering lace 18 and the ankle stabilizing device 10. The centering piece is secured such that the centering lace's central portion is precluded from passing through either of the toe-end pair of eyelets 17'. The centering piece may be attached to the ankle stabilizing device's tongue 60 or to one or both of the front edges of the body member 11. The centering piece may be stitched threads, such as an embroidered trademark, logo, and/or design. Alternatively, the centering piece may include stitched threads, such as an embroidered trademark, logo, and/or design, as well as one or more other elements. In such exemplary embodiments, the centering lace and centering piece may be considered a lace-tongue attachment or a branded lace-tongue attachment. It will be understood that the centering piece may be connected to the device by any number of attachment means such as hook-and-loop fasteners (e.g., for removable attachment), adhesives, complimentary snap devices, buttons, or the like.

In operation, the body member 11 is first placed on the individual's foot. Once the body member 11 is secured to the foot, the centering lace 18 is drawn tight (see FIG. 3) and secured (e.g., by tying the lace 18 into a knot). As noted, the centering lace 18 is attached to the ankle stabilizing device 10. Thus, the individual does not need to re-center the centering lace 18 before drawing it tight and securing it.

To remove the device 10, the centering lace 18 is unsecured (e.g., by untying a knot) and typically un-laced by pulling the centering lace 18 near the toe end 52 of the device 10 such that the free ends 41 of the centering lace 18 pass through all but the last few rows of eyelets 17. For example, FIG. 4 depicts the centering lace 18 un-laced from all of the eyelets 17 except for the toe-end pair of eyelets 17'. After loosening the centering lace 18 in this manner, the device 10 may then be removed from the foot and ankle. In devices according to the present invention, the centering lace 18 does not become uncentered by the removal process because the central portion of the centering lace 18 is attached to the ankle stabilizing device 10 (i.e., via an attachment point 42 or a centering piece).

Accordingly, a subsequent user need only re-lace the portion of the centering lace 18 that has been removed from the eyelets 17 and begin a normal fitting of the device 10. The centering lace 18 will remain centered and not require any centering step.

To supplement the present disclosure, this application incorporates entirely by reference the following commonly assigned patents and patent application publications: U.S. Pat. No. 5,067,486 for an Ankle Stabilizing Appliance (Hely); U.S. Pat. No. 5,795,316 for an Ankle Stabilizing Appliance for Restricting Inversion and Eversion of the Foot (Gaylord); U.S. Pat. No. 7,651,472 for an Ankle Stabilizing Apparatus Having a Pivotable Stiffening Unit (Gaylord et al.); U.S. Patent Publication No. 2005/0288615 A1 for an Ankle Stabilizing Apparatus with Sheet Members Having High Coefficient of Friction filed Jun. 25, 2004 (Gaylord); and U.S. Patent Publication No. 2009/0112140 A1 for an Ankle Stabilizing Apparatus Having a Dynamic Cuff and Stabilizing Strap System filed Apr. 4, 2008 (Gaylord et al.).

In the drawings and specification, there have been disclosed typical embodiments of the invention and, although specific terms have been employed, they have been used in a generic and descriptive sense only and not for purposes of limitation, the scope of the invention being set forth in the following claims. The use of the term "and/or" includes any and all combinations of one or more of the associated listed items.

That which is claimed is:

1. An ankle stabilizing device having a lace attachment, comprising:
    a body member having a front portion, a rear portion, a first side, a second side, an interior surface, and an exterior surface, said first and second sides having free front edges;
    a plurality of eyelets extending along said first and second sides, said plurality of eyelets including a pair of eyelets positioned respectively on said first and second sides; and
    a centering lace having two ends and an attachment point;
    wherein said centering lace's attachment point fixedly secures said centering lace to another portion of the ankle stabilizing device such that said attachment point is precluded from passing through either of said pair of eyelets.

2. The ankle stabilizing device having a lace attachment according to claim 1, wherein said centering lace's attachment point secures said centering lace to another portion of the ankle stabilizing device via stitched threads.

3. The ankle stabilizing device having a lace attachment according to claim 2, wherein said stitched threads are stitched in such a manner as to depict a trademark or design.

4. The ankle stabilizing device having a lace according to claim 1, wherein said centering lace's attachment point secures said centering lace to said first side and/or said second side.

5. The ankle stabilizing device having a lace attachment according to claim 4, wherein said centering lace's attachment point secures said centering lace via stitched threads.

6. The ankle stabilizing device having a lace attachment according to claim 1, wherein said attachment point is positioned between said pair of eyelets.

7. The ankle stabilizing device having a lace attachment according to claim 6, wherein said attachment point is centrally positioned between said pair of eyelets.

8. The ankle stabilizing device having a lace attachment according to claim 1, comprising a tongue positioned between said first and second sides;
    wherein said centering lace's attachment point secures said centering lace to said tongue.

9. The ankle stabilizing device having a lace attachment according to claim 1, wherein said body member is fabricated from substantially inelastic material.

10. The ankle stabilizing device having a lace attachment according to claim 1, wherein said centering lace is configured to pass through said pair of eyelets while said attachment point is precluded from passing through either of said pair of eyelets.

11. An ankle stabilizing device having a lace attachment, comprising:
    a body member having a front portion, a rear portion, a first side, a second side, an interior surface, and an exterior surface, said first and second sides having free front edges;
    a plurality of eyelets extending along said first and second sides, said plurality of eyelets including a pair of opposing eyelets respectively positioned on said first and second sides;
    a centering lace having two ends and a central portion, said central portion defining two substantially equivalent lengths of said centering lace that extend from said central portion to each of said centering lace's ends; and a centering piece fixedly secured to (i) said centering lace and (ii) another portion of the ankle stabilizing device such that said centering lace's central portion is precluded from passing through either of said pair of opposing eyelets.

12. The ankle stabilizing device having a lace attachment according to claim 11, comprising a tongue positioned between said first and second sides;

wherein said centering piece secures said centering lace to said tongue.

13. The ankle stabilizing device having a lace attachment according to claim 12, wherein said centering piece secures said centering lace to said tongue via stitched threads.

14. The ankle stabilizing device having a lace attachment according to claim 13, wherein said stitched threads are stitched in such a manner as to depict a trademark or design.

15. The ankle stabilizing device having a lace attachment according to claim 11, wherein said centering piece secures said centering lace to said first side and/or said second side.

16. The ankle stabilizing device having a lace attachment according to claim 11, wherein said centering piece secures said centering lace via stitched threads.

17. The ankle stabilizing device having a lace attachment according to claim 11, wherein said centering piece is fixedly secured to (i) said centering lace and (ii) another portion of the ankle stabilizing device via a hook-and-loop fastener.

18. The ankle stabilizing device having a lace attachment according to claim 11, wherein said centering lace is configured for its two respective ends to pass through said pair of opposing eyelets while said centering lace's central portion is precluded from passing through either of said pair of opposing eyelets.

19. The ankle stabilizing device having a lace attachment according to claim 11, wherein said centering piece is centrally positioned between said pair of opposing eyelets to fixedly secure said centering lace and another portion of the ankle stabilizing device.

20. An ankle stabilizing device having a lace-tongue attachment, comprising:

a body member having a front portion, a rear portion, a first side, and a second side, said first and second sides having free front edges;

a plurality of eyelets extending along said first and second sides, said plurality of eyelets including a pair of opposing eyelets respectively positioned on said first and second sides;

a tongue positioned between first and second sides of said body member;

a centering lace having two ends and a central portion, said central portion defining two substantially equivalent lengths of said centering lace that extend from said central portion to each of said centering lace's ends; and a centering piece securely attaching said centering lace to said tongue such that said centering lace's central portion is precluded from passing through either of said pair of opposing eyelets.

21. The ankle stabilizing device having a lace-tongue attachment according to claim 20, wherein said centering piece comprises stitched threads securely attaching said centering lace to said tongue.

22. The ankle stabilizing device having a lace-tongue attachment according to claim 20, wherein said centering piece comprises a hook-and-loop fastener securely attaching said centering lace to said tongue.

23. The ankle stabilizing device having a lace-tongue attachment according to claim 20, wherein said centering lace is configured to pass through said opposing pair of eyelets while said centering lace's central portion is precluded from passing through either of said opposing pair of eyelets.

24. The ankle stabilizing device having a lace-tongue attachment according to claim 20, wherein said centering piece securely attaches said centering lace's central portion to said tongue.

* * * * *